United States Patent [19]

Jamas et al.

[11] Patent Number: 4,962,094

[45] Date of Patent: Oct. 9, 1990

[54] GLUCAN DIETARY ADDITIVES

[75] Inventors: Spiros Jamas, Boston; D. Davidson Easson, Jr., Shrewsbury; Bruce R. Bistrian, Ipswich, all of Mass.

[73] Assignee: Alpha Beta Technology, Inc., Worcester, Mass.

[21] Appl. No.: 264,091

[22] Filed: Oct. 28, 1988

[51] Int. Cl.$^5$ ............................................. A61K 31/00
[52] U.S. Cl. ..................................... 514/54; 514/867; 514/892; 514/25
[58] Field of Search ..................... 514/54, 867, 892, 25

[56] References Cited

U.S. PATENT DOCUMENTS

| | | | |
|---|---|---|---|
| 3,867,554 | 2/1975 | Sucher et al. | 426/60 |
| 4,122,196 | 3/1978 | Robbins et al. | 426/60 |
| 4,707,471 | 11/1987 | Larm et al. | 536/1.1 |
| 4,759,942 | 7/1988 | Von Fulger | 426/621 |

OTHER PUBLICATIONS

S. Jamas et al., *Biotechnology and Bioengineering*, 28:769-784 (1986).
Federal Register, vol. 45, No. 174, pp. 58835-58836 (1980).
T. Sakata and W. von Englehardt, *Comp. Biochem. Physiol.*, 74A(2):459-462 (1983).
M. T. Meyer and H. J. Phaff, *Journal of Food Science*, 46:1489-1492 (1981).

*Primary Examiner*—Ronald W. Griffin
*Assistant Examiner*—Everett White
*Attorney, Agent, or Firm*—Hamilton, Brook, Smith & Reynolds

[57] ABSTRACT

Compositions useful in the treatment of dietary disorders, and as dietary additives to provide a source of fiber, of short chain fatty acids and as bulking agents in humans and animals, as well as methods of use therefor. The compositions are based on whole $\beta$-glucans.

11 Claims, 3 Drawing Sheets

GLUCAN DIETARY ADDITIVES

BACKGROUND

Certain natural fibers benefit digestive function, help prevent intestinal and colon cancer and act as fecal gastroenteral bulking agents. Generally, fibers are derived from grains, and are composed of polysaccharides with a range of structures.

Yeast cell walls are largely made up of the hydrophilic polysaccharide beta-glucan. The cell wall is primarily composed of a $\beta(1-3)$ linked glucose polymer with periodic $\beta(1-6)$ linked side chains. A similar polysaccharide can be found in grains, such as barley, which are common sources of dietary fiber.

It is known that a diet high in fiber is beneficial for a variety of reasons. Dietary fiber aids digestion because it provides an indigestible biomass which is carried through the alimentary canal causing undigested food to be pushed out before it. Fiber also clears out bacteria and insures the proper working of the peristaltic muscles. A diet high in fiber has been shown to reduce serum cholesterol and triglyceride levels, and has been linked to lower rates of intestinal and colon cancer. A high fiber diet has also been linked to the reduction of other problems commonly associated with poor digestion, such as ulcer formation, ileitis and colitis.

Dietary fiber is particularly important for persons on a liquid diet, such as, for example, a patient who receives nourishment through a feeding tube due to inadequate function of the gastrointestinal tract, with or without protein calorie malnutrition. A common side effect for those patients who do not receive any fiber supplement is chronic diarrhea due to lack of bulk. This condition may cause depletion of essential nutrients in the patient, dehydration and bowel irritation. Some dietary fibers can be used as a stool or fecal bulking agent to aid digestion and control chronic diarrhea. A fiber having a large water holding capacity is useful for this purpose, because these fibers absorb excess fluid in the colon resulting in increased fecal wet weight and stool number. Furthermore, some fibers are partially digested by bacteria in the large bowel, forming short chain fatty acids, which are preferred energy fuels for the small intestine and improve intestinal function.

Grain $\beta$-glucans are commonly used as a source of fiber. Another source of $\beta$-glucans is yeast cell walls; however, yeast $\beta$-glucans have not been used as a dietary fiber supplement due to the fact that yeast cell wall glucans prepared by traditional methods, such as the method described by Manners et al., in *Biochem. Journal,* 135:19-30 (1973), are not pure, and generally contain materials such as protein, glycogen and chitin. Also, the water-holding capacity of $\beta$-glucans prepared previously is low due to the presence of hydrophobic components such as protein and glycogen, and due to the lack of any three-dimensional cell wall micro-structure. Functionality and purity of a compound to be used for non-irritating, food-grade, fiber preparations are essential to ensure acceptable performance and qualitative properties, such as bland taste and white coloration.

SUMMARY OF THE INVENTION

The present invention is based on the discovery that whole $\beta$-glucans are useful as dietary additives. Dietary supplements containing whole $\beta$-glucans, when administered to mammals, provide a source of fiber in the diet, a fecal bulking agent and a source of short chain fatty acids.

In addition, this invention teaches a method for providing a source of fiber in the diet, for providing a fecal bulking agent and for providing a source of short chain fatty acids by administering whole yeast $\beta$-glucan to an individual. The whole glucans used in this composition and method can be chemically or enzymatically modified, by altering the $\beta(1-6)$ and $\beta(1-3)$ linkages. Partial acid hydrolysis or digestion with enzymes can be used, to modify the $\beta(1-6)$ or $\beta(1-3)$ linkages, respectively. Such modifications are useful to control the water holding capacity of the whole glucan, thereby regulating the degree of gastroenteral bulking.

More importantly, the relative proportions of $\beta(1-6)$ and $\beta(1-3)$ linkages in whole $\beta$-glucan can be altered by genetic modification of the yeast from which it is derived. Mutant cells which exhibit changes in the structure of the yeast cell wall can be isolated by evaluating their resistance to digestion by hydrolytic enzymes. The changes in the structure of the whole $\beta$-glucans may be reflected in the shape of the extracted whole cell walls, in the water-holding characteristics or in the extent of bacterial conversion to short chain fatty acids. Whole $\beta$-glucans extracted from mutant cells can then be used as dietary additives for purposes commensurate with their properties.

The dietary additives of the present invention are based on the three-dimensional matrix structure of whole glucan, which is unique to whole glucan, and cannot be mimicked by other naturally occurring polysaccharides, including other $\beta$-glucan preparations. The composition and method of this invention utilize whole yeast glucan as a dietary additive to improve digestion or treat digestive disorders. For example, the composition can be used to: (1) provide a source of dietary fiber; (2) provide a stool or fecal bulking agent; (3) provide a source of short chain fatty acids via bacterial fermentation in the large bowel, which improves digestion and benefits intestinal and colonic endothelial cells.

The whole $\beta$-glucans of the invention can be administered neat, in a biologically acceptable carrier or as part of a complete nutritional food.

Whole $\beta$-glucans have important properties that make them ideally suited for use as dietary supplements. For example, they have a high water-holding capacity, the water holding capacity can be easily adjusted, and they are highly pure. While $\beta$-glucans provide a number of coincidental, beneficial effects. They provide, in combination, a source of fiber, a fecal bulking agent and a source of short chain fatty acids to improve digestion and stimulate mucosal proliferation in the intestine. Whole $\beta$-glucans are obtained from yeast cell walls using purification process which does not disrupt the three-dimensional cell wall matrix in the process of extracting the non-glucan components, thus enhancing their functionality as a water-absorbing and bulking agent.

DETAILED DESCRIPTION OF THE INVENTION

"Whole β-glucans" are glucans which maintain the intact, the three-dimensional in vivo morphology of the yeast cells from which they are derived. Whole β-glucans are obtained from yeast cell walls using a purification process which does not disrupt the integrity of the cell walls in the process of extracting the non-glucan components.

Figure 1:
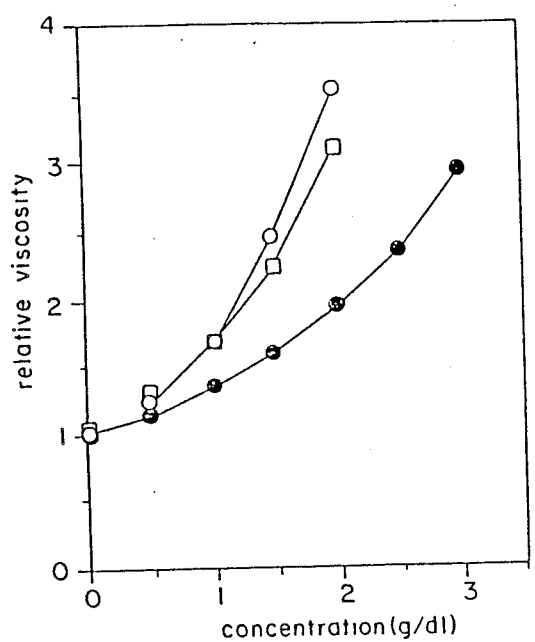
FIG. 1 shows a plot illustrating the viscosity profiles of whole $\beta$-glucans obtained from *Saccharomyces cerevisiae* A364A, 374 and 377.

Whole β-glucans are primarily derived from yeast cell walls. Yeast cell walls are composed predominantly of glucans, which are glucose polymers, having mainly β(1-3) linkages with a smaller component of β(1-6) linkages. Whole β-glucan is the alkali-insoluble portion which can be derived intact from yeast cell walls using the process described by S. Jamas, C. K. Rha and A. J. Sinskey in U.S. patent application Ser. No. 675,927, filed Nov. 28, 1984 entitled "Glucan Compositions and Methods of Preparation Therefor", the teachings of which are incorporated herein by reference. This process yields intact particles of β-glucan, which maintain the spherical, elliptical or rod shaped configuration of the β-glucan as found in vivo, which is referred to as whole glucan. Whole glucan is comparable in size and shape to whole yeast cells, and is composed almost entirely of β-glucan. These hollow, three-dimensional particles are conducive to a high water holding capacity, in that they become filled with water upon hydration. The viscosity of an aqueous solution of whole glucan is indicative of its water holding capacity. Viscosity profiles of β-glucans derived from three different strains of *Saccharomyces cerevisiae* are shown in FIG. 1.

β-glucans obtained using this process are also very pure. The occurrence of other cell wall components, including glycogen, protein and chitin, is minimized when this process is used. Glycogen, protein and chitin are undesirable as the presence of these components tend to reduce the water holding capacity of β-glucans.

Highly pure, whole β-glucans having a very high water holding capacity can be obtained from any yeast strain. For example, the following strains, and mutants or variants derived from them, will yield whole β-glucans: *Saccharomyces cerevisiae, Saccharomyces delbrueckii, Saccharomyces rosei, Saccharomyces microellipsodes, Saccharomyces carlsbergensis, Schizosaccharomyces pombe, Kluyveromyces lactis, Kluyveromyces fragilis, Kluyveromyces polysporus, Candida albicans, Candida cloacae, Candida tropicalis, Candida utilis, Hansenula wingei, Hansenula arni, Hansenula henricii and Hansenula americana*. This whole β-glucan retains the three-dimensional morphology of the yeast cell wall in vivo, since the Jamas et al. extraction process does not cause rupture of the yeast cell walls. The β-glucan product obtained from this process is 96-99% pure; and, since the cell wall structure is intact, it also has a significantly higher water holding capacity than glucans extracted using traditional methods, which lack the intact three-dimensional structure.

Whole yeast β-glucans have several important properties that make them ideally suited to function as dietary supplements. Whole β-glucans are very pure, and exhibit a high water holding capacity. They are wholly composed of glucose units bonded together by β(1-3) and β(1-6) glycosidic linkages, which cannot be degraded by human digestive enzymes, thus making them suitable as a source of dietary fiber. Additionally, as whole β-glucans pass through the large bowel, they can be partially digested by endogenous colonic bacteria without significant loss of their water holding properties. This fermentation process gives rise to short chain fatty acids (predominantly acetate, propionate and butyrate) which are beneficial to mucosal cells lining the intestine and colon. Sakata, T. and Engelhardt, W. V., *Comp. Biochem. Physiol.*, 74a:459–462 (1983).

Whole β-glucans are able to absorb more than ten times their weight in water, which is useful in oral and tube feeding formulations and digestive aids to act as a stool bulking agent, and, thus, as a preventative to diarrhea. For example, whole glucan has a water holding capacity of approximately between 3.0 to 12.0 ml/gram of dry material. Therefore, a typical daily dose for humans of from about 5 to about 50 grams of whole β-glucan can absorb from about 15 to about 600 ml of water from the gastrointestinal tract depending on the desired function for the user. For example, The functional properties of the..whole glucan can be varied between high fiber/low bulking to high fiber/high bulking functions.

The water holding capacity of whole glucan can be altered by genetic, chemical or enzymatic modification, as described by Jamas et al. in U.S. application Ser. No. 675,927; and by Jamas et al., in *Biotechnology and Bioengineering* 28:769–784 (1986) the teachings of which are incorporated herein by reference. Whole glucan can be treated with an acid, such as acetic acid, after its extraction from yeast to reduce the degree of β(1-6) crosslinking, thereby increasing the water holding capacity of the whole glucan. Likewise, treatment with hydrolytic enzymes, such as laminarinase or β(1-3) glucanases reduces the degree of β(1-3) linkages of the whole glucan, resulting in a decrease in the viscosity profile (see FIG. 2) and thus, a decrease in the water holding capacity of whole glucan.

Figure 3:
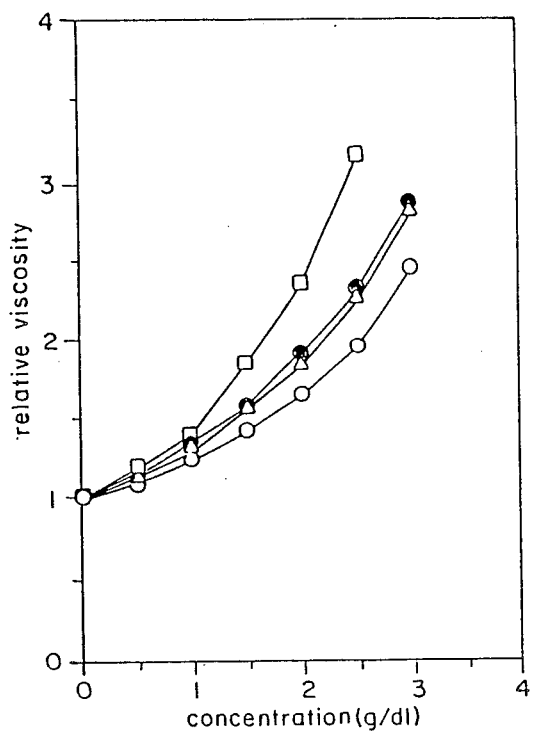
FIG. 3 shows a plot illustrating the viscosity profiles of whole β-glucans obtained from *Saccharomyces cerevisiae* A364A and R4 including viscosity profiles of R4 after treatment with acetic acid and glucanase.
Figure 4:
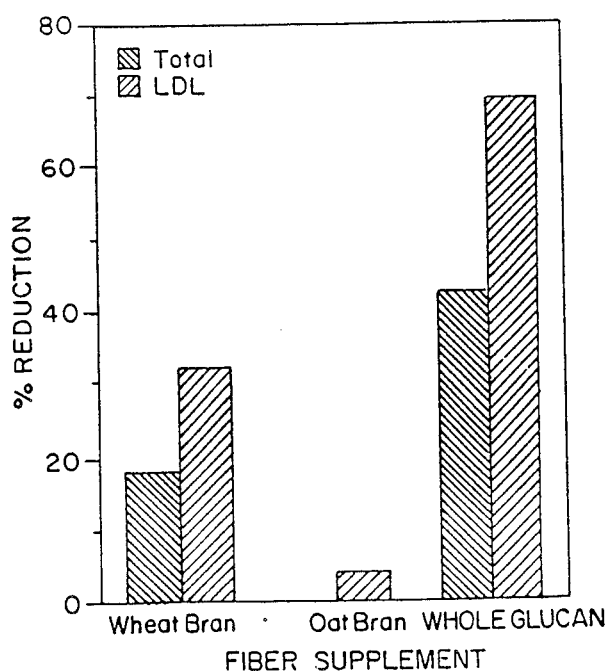

The properties of whole glucan can additionally be altered by genetic modification of the yeast cells from which it is derived. A culture of yeast cells can be induced to mutate by applying a mutating agent, such as ultraviolet radiation, for example. Changes in the structure of the yeast cell wall induced by the mutation can then be evaluated for effect on the morphology and structure of the whole β-glucan extracted from the mutant yeast. These changes may be reflected in the shape of the extracted whole cell walls, the degree of crosslinking, in the viscosity profile (see FIG. 3) which relates directly to water-holding capacity, and/or in the extent of bacterial conversion to short chain fatty acids. β-glucans extracted from the mutant cells can then be used as dietary additives for purposes commensurate with their properties. For example, a mutant strain of *Saccharomyces cerevisiae*, R4 was created by exposing a culture of *Saccharomyces cerevisiae* A364A cells to UV light for 25 seconds, as described by S. Jamas C. K. Rha and A. J. Sinskey in U.S. patent application Ser. No. 166,929 entitled "Glucan Compositions And Process For Preparation Thereof" filed Mar. 11, 1988; and by S. Jamas et al. in *Biotechnology and Bioengineering*, 28:769–784 (1986). R4 shows increased β(1-6) linkages in the glucan structure, which affects its degree of digestibility, and the resultant yield of short chain fatty acids in the large intestine. Mutant yeast cells may be produced by other methods known in the art.

By treating the glucans with mild acids, such as acetic acid, or glucanase enzymes such as laminarinase to alter the $\beta(1-6)$ or $\beta(1-3)$ linkages, respectively, or inducing or isolating mutant yeast strains having altered $\beta$-glucan structures, it is possible to control the hydrodynamic properties of whole glucan, and to control product viscosity precisely for a particular end usage. Therefore, the degree of bulking, for example, can be controlled by administering whole glucan modified to have the desired water holding capacity.

The multiple functionality of whole glucans as a source of short chain fatty acids and as a hydrophilic water absorbing agent makes them valuable as dietary additives acting as a fiber supplement and/or a stool bulking agent that enhances bowel function. Enzymatic modification of whole glucan can allow a range of digestability (from about 15 to about 70% metabolizable glucose) and water holding capacity (from about 3.0 to about 12.0 ml/g of dry material). These properties can be utilized individually or in combination depending on the specific application.

A dietary additive, or supplement, is defined for present purposes as a food material which is administered to or taken by an individual to induce a beneficial or desirable physical effect or to supply one or more components which are missing in the individuals' diet.

The whole glucan preparations can be administered orally, or enterally. The form in which the glucan will be administered (e.g., powder, tablet, capsule, suspension, solution, emulsion) will depend on the patient and the particular treatment. The quantity of the composition to be administered will be determined on an individual basis, and will be based in part on consideration of the condition of the subject, the subject's overall health, and the severity of the disorder being treated. The amount of whole $\beta$-glucans administered to an individual to provide a source of fiber should be the amount necessary to provide all or part of the individual's fiber requirement to aid digestion by providing an indigestible biomass to clear undigested food and debris from the gastrointestinal tract; ensure the proper function of the gastrointestinal tract; prevent dehydration and/or bowel irritation in the individual; clear out bacteria and aid proper working of the peristaltic muscles; prevent diarrhea, which can occur when there is insufficient fiber in the diet; and/or to reduce serum cholesterol and triglyceride levels. The amount of whole $\beta$-glucans administered to an individual as a bulking agent should be the amount necessary to provide water-adsorbing bulk to prevent dehydration and bowel irritation in the individual; to aid digestion; and to increase fecal wet weight and stool number, and to thereby control chronic diarrhea caused by excess fluid in the digestive system. The amount of whole $\beta$-glucans administered to an individual as a source of short-chain fatty acids should be the amount necessary to aid digestion and improve intestinal function and stimulate proliferation of mucosal cells in the intestines. For example, dosage levels can be from about 5 to about 50 grams of whole $\beta$-glucan per day; and will generally range from about 30 to about 40 g of whole $\beta$-glucans per day to provide a source fiber in the diet and/or as a bulking agent.

The composition may be administered orally, in liquid or solid form, either at room temperature or chilled, or enterally through a feeding tube. Glucan as a source of fiber can be administered alone, in a biologically acceptable carrier (e.g., saline or water) with other ingredients such as vitamins and minerals, or as part of a complete-nutritional food. For example, whole glucan can be administered as a component in a high fiber liquid food for oral or enteral feeding, by continuous or intermittent drip into a feeding tube (e.g., nasogastric, nasoduodenal, jejunal). Liquid formulations generally contain about 5.0 g whole glucan per 8 fluid ounces.

The composition of the present invention can optionally include, in addition to whole $\beta$-glucan, other components, which will be determined primarily by the manner in which the composition is to be administered. For example, a composition to be administered orally in tablet or powder form can include, in addition to whole $\beta$-glucan, a filler (e.g., corn starch, sucrose, lactose), a binder (e.g., carboxymethyl cellulose, gum arabic, gelatin), an adjuvant, a flavoring agent, a coloring. agent, and/or a coating material (e.g., wax or plasticizer) and-/or other nutritional supplements. A composition to be administered in liquid form can include whole $\beta$-glucan and, optionally, an emulsifying agent, a diluent (e.g., water, sterile saline) and/or a coloring or flavoring agent, or combined in a complete feeding formula to be administered orally or by feeding tube into the digestive tract. A complete feeding formula can contain all nutritional requirements. For example, such a feeding formula for oral or enteral administration could contain whole glucan (as the source of dietary fiber), water, a source of carbohydrate (e.g., sucrose, hydrolyzed corn starch), an oil (e.g., corn or soybean oil), selected sources of vitamins (e.g., choline chloride, ascorbic acid, alpha-tocophenyl acetate, niacinamide, calcium pantothenate, thiamine, riboflavin, phylloquinone, cyanocobalamin, vitamin $D_3$); selected sources of minerals (e.g., potassium citrate, magnesium chloride, calcium phosphate tribasic, sodium citrate, potassium chloride, zinc sulfate, ferrous sulfate, manganese sulfate, cupric sulfate); a source of protein (e.g., soy protein isolate, calcium caseinate), and lecithin.

For a complete nutritional liquid food, to be used as the sole source of nutrition, the dosage for an average adult can be between about 1500-2000 calories per day. A complete nutritional formulation can have the following caloric distribution:

Liquid Nutrition Plus Fiber—Enteral Feeding
Complete Nutritional Formulation

| Liquid Nutrition Plus Fiber - Enteral Feeding Complete Nutritional Formulation | | |
|---|---|---|
| Contents | Grams/Liter | % of Total Calories |
| Protein | 20-60 | 8-23 |
| Fat | 1-100 | 1-90 |
| Carbohydrate | 40-220 | 20-91 |
| Glucan | 10-50 | 0-10 |
| Vitamins* | RDA | 0 |
| Minerals* | RDA | 0 |
| Water | 800-950 | 0 |

*Provide recommended dietary allowance of all essential vitamins and minerals

For most individuals the calorie distribution can be: about 14-15% protein, about 30-32% fat and about 53-56% carbohydrate.

The invention is illustrated further by the following examples, which are not to be taken as limiting in any way.

EXAMPLE 1

Composition of Whole β-glucans From Strains Saccharomyces Cerevisiae A364A and R4

Whole β-glucan was extracted from strains *Saccharomyces cerevisiae* A364A and R4 according to the process described in U.S. patent application Ser. No. 675,927 by S. Jamas, C. K. Rha and A. J. Sinskey entitled, "Glucan Compositions and Methods of Preparation Therefor", filed Nov. 28, 1984.

Protein and hexose content of whole glucans

Protein content of the whole β-glucans was determined chemically using the Bio-Rad assay (Bio-Rad, Richmond, Calif.). In this procedure, glucan samples were suspended in water to a concentration of 5 mg/ml, and lysozyme solutions in the range of 0.2 to 1.0 mg/ml were prepared as standards. Duplicate 0.1 ml aliquots of the samples and standards were placed in clean, dry test tubes and 5.0 ml of the diluted dye reagent was added. The solutions were vortexed, and after 5 minutes, the optical density (OD.) was measured at 595 nm. A water blank was used as a negative control.

Total hexose was measured in duplicate 100-fold dilutions of the glucan suspensions. A standard curve was prepared using glucose solutions in the range of 10–100 ug/ml. Duplicate 1 ml aliquots of the samples were placed in clean, dry test tubes and 1 ml of 5% (v/v) phenol was added. Then, 5 ml of concentrated sulfuric acid ($H_2SO_4$) was added to each tube, the mixture was vortexed, and incubated at 37° C. for 15–20 minutes. The optical density was measured at 488 nm with a water sample as the blank. The results are shown in Table 1.

TABLE 1

| | Protein Content | | | |
|---|---|---|---|---|
| Preparation | Protein mg/ml | Hexose mg/ml | Hexose/Protein Ratio | % Protein |
| A364A | 0.071 | 8.74 | 123:1 | 0.80 |
| R4 | 0.082 | 8.81 | 108:1 | 0.91 |

Chitin and Glycogen Content

Fourier-Transform Infrared (FT-IR) spectroscopy was used to detect the presence of chitin and glycogen, and peak integration was used to determine their relative levels. The characteristic glycogen peaks, which appear at a wave number of 850, 930 and 760 $cm^{-1}$, were not detected in the whole β-glucan preparations, but were clearly present in the glucans extracted using an alternate process described by Manners et al. in *Biochem. J.*, 135:19–30 (1973). In addition the characteristic chitin peak, which appears at a wave number of 1550 $cm^{-1}$ was significantly stronger in the Manners' preparation. The results are shown in Table 2.

TABLE 2

| CONTAMINANT LEVELS DETECTED BY FT-IR SPECTOSCOPY | | |
|---|---|---|
| Contaminant | Whole Glucan | Manner's Prep. |
| Glycogen | 1.0 | 9.4 |
| Chitin | 1.0 | 2.9 |

Manner's preparation contains an approximately 10-fold higher level of glycogen, and a 3-fold higher level of chitin over the whole glucan preparation. Table 3 illustrates the significant compositional difference resulting from these procedures:

TABLE 3

| COMPARISON OF BETA-GLUCAN PREPARATIONS | | | | |
|---|---|---|---|---|
| Component | Whole glucan | | Manner's Prep. | |
| Content | mg | % | mg | % |
| Glucan | 1000 | 96.2 | 1000 | 51.8 |
| Protein | 2 | 0.8 | 351 | 18.2 |
| Glycogen | 31 | 2.9 | 579 | 30.0 |

Based on 1000 mg samples of glucan, the whole glucan sample contained only 33 mg of contaminants, whereas the Manners' preparation contained 930 mg. The contaminant mass displaces its weight in water from the glucan particles, so that the contaminated glucan has a considerably lower water holding capacity.

EXAMPLE 2

Treatment of Whole Glucan With Acetic Acid

Five hundred mg samples of whole glucan from *S. cerevisiae* prepared as described in Example 1, from strains 374, 377 and R4, were suspended in 250 ml of 0.5 M acetic acid. The suspensions were continuously stirred at 90° C. for 3 hours. At the end of this extraction, the remaining insoluble glucan residue was recovered by batch centrifugation at 5000 rpm for 20 minutes. The glucan residue was washed once in 200 ml distilled water, once in 200 ml dehydrated ethanol and twice in 200 dehydrated ethyl ether. The resulting slurry was dried in air at 37° C. for 12 hours. The initial suspension in acetic acid and the supernatant were assayed for total carbohydrate content to determine the proportion of the extractable β(1–6) glucan component. The white glucan powder obtained after drying was resuspended in distilled water to determine its viscosity profile (see FIG. 3). The results are shown in Table 4. As indicated by the results, the mild acid treatment ±increases the water holding capacity of the whole glucans by approximately 20% and therefore will have a commensurate effect on their bulking properties.

TABLE 4

| Viscosity Profiles of Glucans Before and After Acetic Acid Treatment | | | | |
|---|---|---|---|---|
| Yeast | Viscosity in Centipoise, 25° C. | | | |
| Strain | 2% | 2.5% | 3% | 3.5% |
| *Saccharomyces cerevisiae* | | | | |
| 374 (before) | 1.5 | 2.8 | 7.1 | 14.2 |
| 374 (after) | 1.6 | 4.7 | 58.3 | 1879.0 |
| 377 (before) | 1.6 | 3.4 | 16.0 | 75.0 |
| 377 (after) | 1.7 | 4.7 | 58.3 | 1878.0 |
| R4 (before) | 1.8 | 2.3 | 3.1 | 4.5 |
| R4 (after) | 2.6 | 4.6 | 12.4 | 106.3 |

EXAMPLE 3

Treatment of Whole Glucan with Laminarinase

Four hundred mg samples of whole glucan from *Saccharomyces cerevisiae* prepared as described in Example 1, from strains A364A, 374 and 377, were suspended in 400 ml of distilled water. Laminarinase (endo β(1–3) glucanase) (Sigma Chemical Co.) in a concentration of 0.25 mg/ml in phosphate buffer at pH 7.0 was added. The solutions were incubated at 37° C. for 4 hours. At the end of the incubation the solutions were held at 70° C. for 15 minutes to deactivate the enzyme. The remaining residue was recovered by centrifugation at 5000 rpm for 20 minutes. The resulting glucan residues were diluted into a range of concentrations in order to obtain viscosity measurements of the laminarinase degraded glucan samples. Since the enzyme cannot be effectively removed from solution, a control experiment was performed as above containing the enzyme only. The readings from the control were used to correct the solvent viscosity accounting for the contribution of the enzyme to the macroscopic viscosity of the suspension. The results are shown in Table 5.

TABLE 5

Viscosity Profile of Glucans Before and After Treatment with Laminarinase

| Yeast Strain | Viscosity in Centipoise, 25° C. | | | |
|---|---|---|---|---|
| | 1% | 2% | 3% | 3.5% |
| Saccharomyces Cerevisiae | | | | |
| A364A (before) | 1.4 | 2.7 | 13.7 | 127.3 |
| A364A (after) | 1.2 | 1.6 | 3.1 | 6.4 |
| 374 (before) | 1.6 | 4.0 | 47.4 | 2630.7 |
| 374 (after) | 1.3 | 2.3 | 9.3 | 62.9 |
| 377 (before) | 1.6 | 3.4 | 16.0 | 75.0 |
| 377 (after) | 1.4 | 2.8 | 18.1 | 367.3 |

Figure 2:
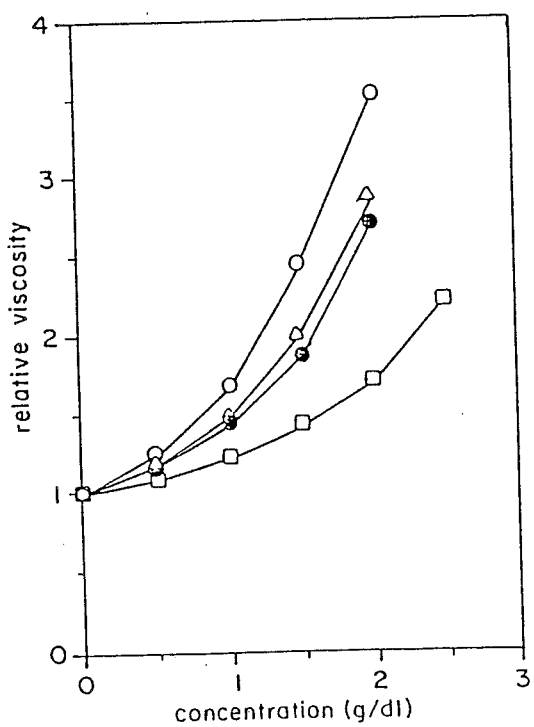
FIG. 2 shows a plot illustrating the viscosity profiles of whole $\beta$-glucan obtained from *Saccharomyces cerevisiae* A364A and 374 before and after treatment with laminarinase.

FIG. 2 shows the viscosity profile of glucan derived from strain A364A before and after a 4 hour laminarinase digest. Digestion of whole glucans with hydrolytic enzymes such as laminarinase will partially degrade their three-dimensional matrix structure thereby reducing their water-holding capacity. This procedure is employed to produce β-glucans with high fiber/low bulking function.

EXAMPLE 4

Modification of Whole Glucan Cell Wall Structure Through Genetic Modification of the Producing Strain The following procedure is employed to produce and isolate mutant yeast cells having altered cell wall structures: Saccharomyces cerevisiae A364A is used in this example, however, other yeast strains may be used.

Strain A364A was grown in 100 ml YPD to mid-log phase. The cells were washed in buffer and divided into aliquots of approximately 5 ml in sterile glass petri plates. A UV exposure of 25 sec (30% survival) was used as the mutagenesis procedure. The cells were then suspended in 5 ml YEPD (1% yeast extract, 2% bacto peptone, 2% glucose) and grown under subdued light to a concentration of 5×10⁶ CFU/ml. The cells were harvested, and protoplasts were prepared using 0.25 mg/ml laminarinase for 30 minutes. The suspension was then diluted with water to lyse osmotically sensitive protoplasts. The surviving cells then were grown in 5 ml YPD to density of approximately 5×10⁶ CFU/ml. The laminarinase treatment was repeated two more times using 1.0 mg/ml enzyme for 15 minutes. The candidates which resistance to laminarinase digestion were then streaked on YEPD agar (1.5%) plates. Single colony isolates were tested for resistance to the enzyme compared to the resistance of the control strain, A364A. The mutant referred to as R4, is available from the Agricultural Research Service under No. NRRL Y-15903. The water holding capacity of whole β-glucan derived from Saccharomyces Cerevisiae strains A364A and R4 is shown in Table 6.

TABLE 6

The Water Holding Capacity of Genetically Modified (R-4) and Unmodified (A364A) Whole Glucans

| Yeast Strain | Treatment | Water-holding capacity (ml/g dry material) |
|---|---|---|
| A364A | none | 9.2 |
| A364A | acetic acid | 9.0 |
| A364A | laminarinase | 5.7 |
| R4 | none | 8.9 |
| R4 | acetic acid | 10.3 |
| R4 | laminarase | 7.1 |

EXAMPLE 5

A Complete High-Fiber Liquid Food Containing Whole β-Glucan

A high fiber liquid food for oral or enteral feeding was formulated using whole glucan as the source of dietary fiber. The composition contained the following ingredients: distilled water, hydrolyzed corn starch, sucrose, sodium and calcium caseinates, corn oil, whole glucan, minerals (potassium citrate, magnesium chloride, calcium phosphate tribasic, sodium citrate, potassium chloride, zinc sulfate, ferrous sulfate, manganese sulfate, cupric sulfate), soy protein isolate, flavorings, soy lecithin and vitamins (choline chloride, ascorbic acid, alpha-tocophenyl acetate, niacinamide, calcium pantothenate, thiamine chloride hydrochloride, pyridoxine hydrochloride, riboflavin, vitamin A palmitate, folic acid, biotin, phylloquinone, cyanocobalamin, vitamin $D_3$).

The formulation was prepared by adding the following components to 4 fl. oz. of distilled water:

| Contents | grams |
|---|---|
| Sodium caseinate | 3.5 |
| Calcium caseinate | 5.9 |
| Corn Oil | 8.8 |
| Sucrose | 7.0 |
| Whole β-glucan | 5.0 |
| Hydrolyzed corn starch | 26.3 |

The following vitamins and minerals were added:

| | |
|---|---|
| Vitamin A | 850 I.U. |
| Vitamin D | 68 I.U. |
| Vitamin E | 7.7 I.U. |
| Vitamin K | 12 mcg |
| Vitamin C | 51 mg |
| Folic Acid | 102 mcg |
| Thiamine (Vitamin $B_1$) | 0.39 mg |
| Riboflavin (Vitamin $B_2$) | 0.44 mg |
| Vitamin $B_6$ | 0.51 mg |
| Vitamin $B_2$ | 1.6 mcg |
| Niacin | 5.1 mg |
| Choline | 102 mg |
| Biotin | 77 mcg |
| Pantothenic Acid | 2.55 mg |
| Sodium | 200 mg |
| Potassum | 370 mg |
| Chloride | 340 mg |
| Calcium | 170 mg |
| Phosphorous | 170 mg |
| Magnesium | 68 mg |
| Iodine | 25.5 mcg |
| Manganese | 0.85 mg |
| Copper | 0.34 mg |
| Zinc | 3.83 mg |
| Iron | 3.06 mg |

All components were mixed until dissolved or suspended in a homogeneous mixture, and enough additional water was added to bring the volume to 8 fl. oz.

EXAMPLE 6

A Bulk Laxative Containing Whole β-Glucan

A bulk laxative was formulated by adding 5.0 g of whole β-glucan to 8 oz. of cold water, and stirring until the β-glucan was suspended in the water. This formulation can then be administered orally to a patient, up to 3 times daily to provide a laxative effect.

EXAMPLE 7

Method to Control the Bulking Properties of Whole Glucans by Chemical Modification The bulking properties of the whole glucans are a direct function of their hydrodynamic volume. However, degradation of the glucan matrix by hydrolytic enzymes present in the large intestine may significantly impair this property. It is therefore important to control the bulking properties and degradation of the glucan particles for a variety of applications.

Glucan particles were prepared according to the method of Jamas et al (USSN 675,927) from *Saccharomyces cerevisiae* 377. A portion of the glucan particles was further extracted by suspending 500mg of the glucan in 250ml of 0.5M acetic acid and stirring for 3 hours at 90° C. The whole glucan and the acetic extracted glucan were digested with a mixture of hydrolytic enzymes containing β(1-4), β(1-3) and β(1-6) glucanase activities to simulate the conditions that the glucan will be exposed to in the large intestine. The bulking properties of the glucan before and after digestion were measured as was the amount of glucose released and the percent undigested fiber (see Table 7).

TABLE 7

Properties of Whole Glucans Before And After Digestion

| PRODUCT | Initial Water Holding Capacity (ml/gram) | Final Water Holding Capacity (ml/gram) | Digestable Glucose (mg/gram) | % Undigested Glucan |
| --- | --- | --- | --- | --- |
| Untreated 377 | 9.1 | 6.5 | 250 | 75 |
| 377/acetic acid | 10.3 | 4.1 | 600 | 40 |

The two products, untreated 377 and 377 treated with acetic acid behave significantly differently under simulated conditions. The results show that the whole glucan, 377, will provide high bulking properties throughout its residence in the intestine and does not degrade significantly. The acetic acid-treated material is more susceptible to enzymatic hydrolysis, yielding a higher quantity of metabolizable glucose per gram of fiber (Table 8). In this case, the product will benefit patients with impaired bowel function in which the fiber will provide a low bulking component and considerable nutrition to the epithelial cells.

EXAMPLE 8

Method to Control Degradation of Whole Glucans By Modifying the Ratio of β(1-6) to β(1-3) Linkages The whole glucans consist of β(1-3)-linked glucose backbone chains with periodic β(1-6) branching. The relative ratio of the β(1-6) to β(1-3) linkages in the glucan matrix determines its resistance to digestion by hydrolytic enzymes. The employment of mutant or genetically engineered strains with altered β(1-6) linkages result in whole glucans with a range of properties as dietary fiber.

To demonstrate this, whole glucans from *Saccharomyces cerevisiae* strain A364A, and the mutant strain R4, were digested with a mixture of hydrolytic enzymes to simulate the conditions in the intestine. The results, shown in Table 8, illustrate how the ratio of linkages in the whole glucan can be used to produce a high bulking/low digestible fiber or a low bulking/high digestible fiber.

TABLE 8

The Effect of Linkage Ratio in Whole Glucans on their Function as a Dietary Fiber

| PRODUCT | Initial Water Holding Capacity (ml/gram) | Final Water Holding Capacity* (ml/gram) | Digestable Glucose (mg/gram) |
| --- | --- | --- | --- |
| A364A | 9.2 | 5.0 | 550 |
| R4 | 8.7 | 7.1 | 225 |

*After enzymatic digestion

The results above demonstrate how the A364A whole glucan is degraded considerably by the hydrolytic enzymes providing a high level of metabolizable glucose representing approximately 50% of ? .! 15 the total fiber. The modified whole glucan of strain R4, which has an increased ratio of β(1-6) to β(1-3) linkages, is more resistant to the hydrolytic enzymes thus maintaining over 80% of its bulking properties and providing a lower quantity of metabolizable glucose.

Equivalents

Those skilled in the art will recognize, or be able to ascertain using no more than routine experimentation, many equivalents to the specific embodiments of the invention described herein. Such equivalents are intended to be encompassed in the scope of the following claims.

We claim:

1. A method of providing a source of fiber in the diet of a mammal comprising administering to the mammal an amount of whole yeast β-glucan sufficient to aid digestion, reduce dehydration or reduce the serum cholesterol level in the mammal.

2. A method of claim 1 wherein the whole yeast β-glucan is in a biologically acceptable carrier.

3. A method of claim 2 wherein the carrier is sterile saline or water, and the composition is administered orally or through a feeding tube.

4. A method of claim 2 wherein the whole yeast β-glucan is administered to the mammal as part of a complete nutritional food formulaton.

5. A method of claim 1 wherein the bulking and digestibility of the fiber is altered by increasing or decreasing the relative proportion of β(1-3) and β(1-6) linkages.

6. A method of providing a fecal bulking agent to a mammal comprising administering to the mammal an amount of whole yeast β-glucan sufficient to absorb excess water thereby reducing dehydration, bowel irritation and chronic diarrhea in the mammal.

7. A method of claim 6 wherein the whole yeast β-glucan is in a biologically acceptable carrier.

8. A method of claim 7 wherein the carrier is sterile saline solution or water, and the composition is administered orally or through a feeding tube.

9. A method of claim 7 wherein the whole yeast β-glucan is administered to the mammal as part of a complete nutritional feed.

10. A method of providing a source of short chain fatty acids to a mammal comprising administering to the mammal an amount of whole yeast β-glucan sufficient to aid digestion in improved intestinal function.

11. A method of treating gastroenteral disorders and improving digestion in mammals comprising administering to the mammal a quantity of whole yeast β-glucan sufficient to provide a source of short chain fatty acids.

* * * * *